United States Patent [19]

Hess et al.

[11] Patent Number: 5,928,271
[45] Date of Patent: Jul. 27, 1999

[54] ATRIAL ANTI-ARRHYTHMIA PACEMAKER AND METHOD USING HIGH RATE ATRIAL AND BACKUP VENTRICULAR PACING

[75] Inventors: Michael F. Hess, Minneapolis; Kathleen A. Prieve, Shoreveiw, both of Minn.

[73] Assignee: Medtronic, Inc., Minneapolis, Minn.

[21] Appl. No.: 09/030,312

[22] Filed: Feb. 25, 1998

[51] Int. Cl.[6] .......................... A61N 1/368; A61N 1/365; A61N 1/362
[52] U.S. Cl. .................................. 607/14; 607/4
[58] Field of Search ........................................ 607/14, 4

[56] References Cited

U.S. PATENT DOCUMENTS

| | | |
|---|---|---|
| 4,316,472 | 2/1982 | Mirowski et al. . |
| 4,375,817 | 3/1983 | Engle et al. . |
| 4,384,585 | 5/1983 | Zipes . |
| 4,543,963 | 10/1985 | Gessman . |
| 4,577,633 | 3/1986 | Berkovits et al. . |
| 4,587,970 | 5/1986 | Holley et al. . |
| 4,726,380 | 2/1988 | Vollman et al. . |
| 4,727,877 | 3/1988 | Kallok . |
| 4,800,883 | 1/1989 | Winstrom . |
| 4,830,006 | 5/1989 | Haluska et al. . |
| 4,880,005 | 11/1989 | Pless et al. . |
| 4,949,719 | 8/1990 | Pless et al. . |
| 4,953,551 | 9/1990 | Mehra et al. . |
| 5,117,824 | 6/1992 | Keimel et al. . |
| 5,163,427 | 11/1992 | Keimel . |
| 5,188,105 | 2/1993 | Keimel . |
| 5,269,298 | 12/1993 | Adams et al. . |
| 5,653,737 | 8/1997 | van Lake . |
| 5,788,717 | 8/1998 | Mann et al. . |

FOREIGN PATENT DOCUMENTS 9202829  10/1992  WIPO .

OTHER PUBLICATIONS

"Onset and Stability for Ventricular Tachyarrhythmia Detection in an Implantable Pacer–Cardioverter–Defibrillator", Olson et al, *Computers in Cardiology*, Oct. 7–10, 1986, IEEE Computer Soc. Press, pp. 167–170.

"Automatic Tachycardia Recognition", Arzbaecher et al, *PACE*, May–Jun., 1984, pp.541–547.

*Primary Examiner*—William E. Kamm
*Assistant Examiner*—Carl H. Layno
*Attorney, Agent, or Firm*—Reed A. Duthler; Harold R. Patton

[57] ABSTRACT

An atrial and ventricular pacemaker including an atrial pulse generator having the capability of delivering high rate atrial pacing pulses for electrophysiologic study and having the capability of delivering ventricular pacing pulses as a backup, during delivery of high rate atrial pacing pulses. Delivery of backup ventricular pacing pulses may be preconditioned upon the occurrence of a desired number, proportion or pattern of occurrences of paced ventricular beats preceding delivery of high rate atrial pacing pulses. Timing of ventricular backup pulses is synchronized to delivered atrial pacing pulses which occur closely timed to expiration of a defined ventricular escape interval for backup pacing. The defined escape interval for ventricular backup pacing may be set as a function of the average interval separating ventricular events preceding initiation of high rate atrial pacing.

20 Claims, 6 Drawing Sheets

ATRIAL ANTI-ARRHYTHMIA PACEMAKER AND METHOD USING HIGH RATE ATRIAL AND BACKUP VENTRICULAR PACING

BACKGROUND OF THE INVENTION

The present invention relates to medical stimulators and leads generally, and more particularly to implantable atrial anti-arrhythmia pacemakers.

In conjunction with stimulators which treat atrial arrhythlnias, it is often beneficial to include the capability of delivering high rate atrial pacing pulses, either for therapeutic purposes to terminate detected atrial arrhythmias or for electrophysiologic screening purposes to induce and terminate arrhythmias under physician control. In most patients, during an atrial tachyarrhythmia or during rapid atrial pacing, atrial depolarizations are effective to trigger ventricular depolarizations sufficient to provide a ventricular rate adequate to support the patient. However, in the context of patients having total or intermittent AV block, their ventricular rate may drop to an extremely low level during atrial anti-tachycardia pacing or during rapid atrial stimulation for testing purposes, in the absence of backup ventricular pacing. For this reason, atrial anti-tachycardia pacemakers and defibrillators have employed ventricular back-up pacing in conjunction with rapid atrial pacing.

For example, during temporary high rate atrial pacing, the Intermedics Relay TM pacemaker can provide ventricular pacing at a selected multiple of the atrial escape interval. In other words, in the presence of rapid atrial pacing, a ventricular pacing pulse may be delivered once every X atrial pacing pulses. A similar feature is available in the Medtronic Thera® pacemaker, presently marketed by Medtronic.

In defibrillators, it has also been proposed to provide ventricular back-up pacing in conjunction with rapid atrial pacing used for electrophysiologic screening purposes. For example, demand VVI pacing as a backup to rapid atrial pacing is provided in the Ventak AV Model 1810 and 1815 implantable cardioverter/defibrillators presently sold by Cardiac Pacemakers, Inc. Back-up VVI pacing is also proposed in U.S. Pat. No. 5,653,737 issued to van Lake.

The back-up ventricular pacing provided in the Intermedics Relay and Medtronic Thera® devices is asynchronous to the underlying ventricular rhythm, the ventricular sense amplifier being disabled during delivery of rapid atrial pacing pulses. In the Ventak AV, however, ventricular demand pacing is provided at a programmed pacing rate, as also suggested in the above cited U.S. Pat. No. 5,653,737. In both of these patents, however, the escape interval is apparently set independent of the delivery of atrial pacing pulses as well as independent of the underlying ventricular rate of the patient. In the context of providing back-up ventricular pacing during rapid atrial pacing, however, it should be noted that sensing ventricular depolarizations may often be difficult due to the requirement that the ventricular sense amplifier be blanked in conjunction with delivery of atrial pacing pulses. Due to the difficulty of sensing in the ventricle during delivery of high rate atrial pacing pulses, the potential for competition between delivered ventricular pacing pulses and the patient's underlying ventricular rate remains substantial using either approach.

SUMMARY OF THE INVENTION

The present invention is directed to providing backup ventricular pacing during high rate atrial pacing using a simple, automatic pacing modality which provides backup pacing where necessary, avoids ventricular competition when possible, and in addition allows for synchronization of the delivered ventricular pacing pulses to delivered high rate anti-tachycardia pacing pulses. The present invention accomplishes these results by means of either a VOO (asynchronous) or VVI (inhibited) ventricular pacing modality.

In the context of the VOO mode of operation of the present invention, the stimulator employs the ventricular intervals (V-V intervals) prior to initiation of high rate ventricular pacing to determine a desired ventricular escape interval for back-up ventricular pacing. This may be the average V-V interval over the preceding sequence of ventricular events or the average V-V interval minus a decrement. A-A intervals separating delivered atrial pacing pulses are then successively added to a running interval total on delivery of each atrial pulse. When the running interval total is greater than or equal to the desired ventricular escape interval, a short ventricular escape interval is initiated, for example 30 milliseconds, on the expiration of which a ventricular pacing pulse is delivered. Thus, the effective ventricular escape interval for backup pacing corresponds generally to the underlying ventricular rate prior to high rate atrial pacing, automatically adjusted to slightly follow a delivered atrial pulse. In order to avoid ventricular competitive pacing whenever possible, when a device according to the present invention operates in the VOO mode, it preferably requires that a defined percentage of the preceding series of ventricular events must have been paced events as a prerequisite to activating ventricular backup pacing during rapid atrial pacing. For example, the device may require that all four of the preceding four ventricular events were paced ventricular events, with ventricular backup pacing disabled in the presence of a single sensed ventricular event. Alternatively, other percentages, proportions or patterns of occurrences of paced ventricular events over the of the preceding series of ventricular events may be required to allow ventricular backup pacing during high rate atrial pacing.

In the case of the present invention operating in VVI or inhibited mode, the desired escape interval for ventricular backup pacing may be a programmed, pre-set value. Determination of the time of delivery of the ventricular pacing pulse occurs identically, to the VOO mode, by adding successive A-A intervals to a running interval total on delivery of atrial pacing pulses and comparing the running total with the desired escape interval. In addition, the running interval total is reset to zero on occurrence of a sensed ventricular event during delivery of atrial high rate pacing. When a device according to the present invention operates in the VVI mode, it may optionally also require that a defined percentage of the preceding ventricular events must have been paced events as a prerequisite to activating ventricular backup pacing during rapid atrial pacing.

DETAILED DESCRIPTION OF THE PREFERRED EMBODIMENT

Figure 1:
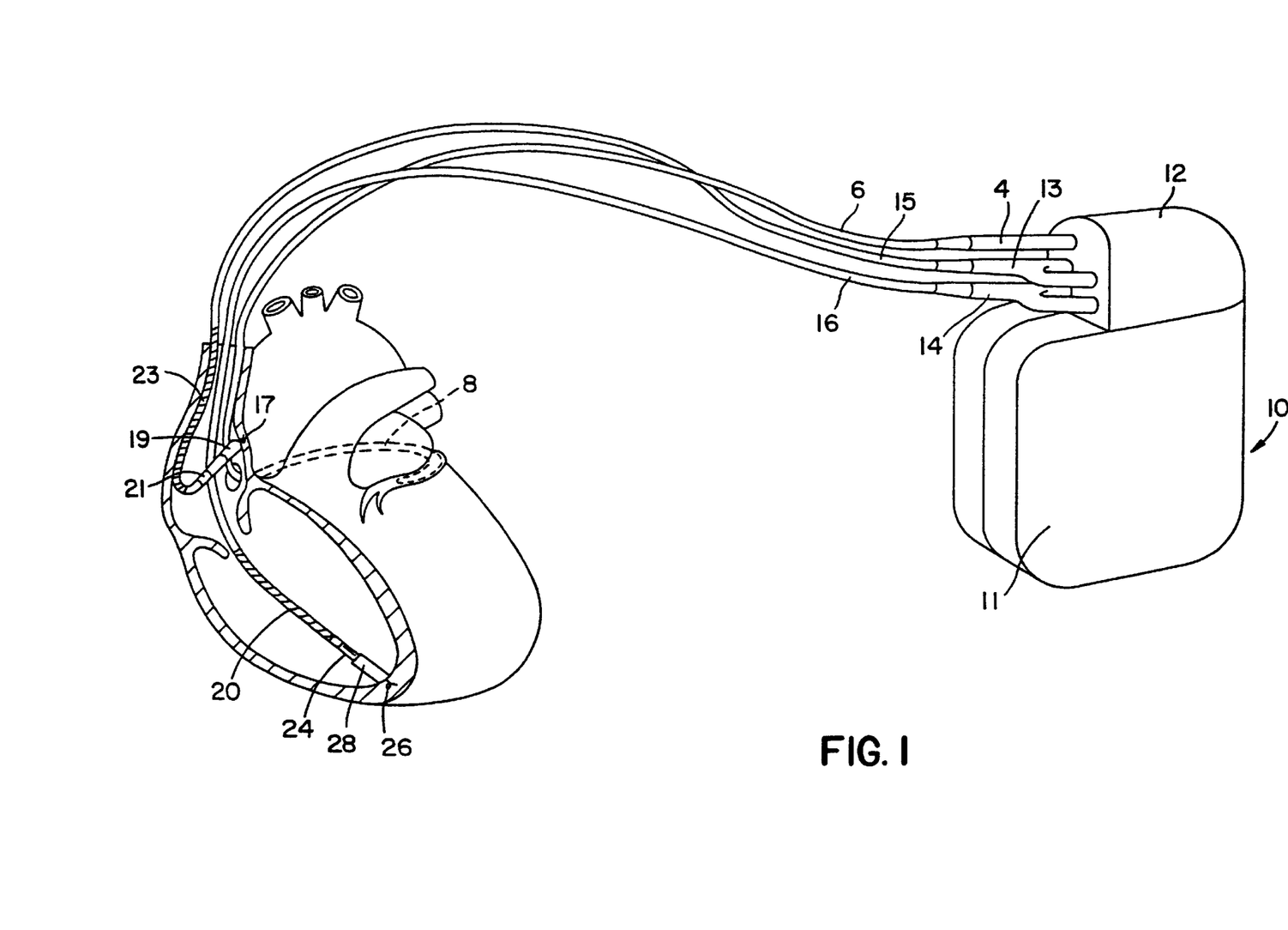
FIG. 1 illustrates a first embodiment of an implantable anti-arrhythmia stimulator system according to the present invention.

FIG. 1 illustrates an anti-arrhythmia stimulator system incorporating the present invention. The ventricular lead includes an elongated insulative lead body 16, carrying three concentric coiled conductors, separated from one another by tubular insulative sheaths. Located adjacent the distal end of the lead are a ring electrode 24, an extendable helix electrode 26, mounted retractably within an insulative electrode head 28, and an elongated coil electrode 20. Each of the electrodes is coupled to one of the coiled conductors within the lead body 16. Electrodes 24 and 26 are employed for cardiac pacing and for sensing ventricular depolarizations. At the proximal end of the lead is a bifurcated connector 14 which carries three electrical connectors, each coupled to one of the coiled conductors.

The atrial/SVC lead includes an elongated insulative lead body 15, carrying three concentric coiled conductors, separated from one another by tubular insulative sheaths, corresponding to the structure of the ventricular lead. Located adjacent the J-shaped distal end of the lead are a ring electrode 21 and an extendable helix electrode 17, mounted retractably within an insulative electrode head 19. Each of the electrodes is coupled to one of the coiled conductors within the lead body 15. Electrodes 17 and 21 are employed for atrial pacing and for sensing atrial depolarizations. An elongated coil electrode 23 is provided, proximal to electrode 21 and coupled to the third conductor within the lead body 15. At the proximal end of the lead is a bifurcated connector 13 which carries three electrical connectors, each coupled to one of the coiled conductors.

The coronary sinus lead includes an elongated insulative lead body 6, carrying one coiled conductor, coupled to an elongated coiled defibrillation electrode 8. Electrode 8, illustrated in broken outline, is located within the coronary sinus and great vein of the heart. At the proximal end of the lead is a connector plug 4 which carries an electrical connector, coupled to the coiled conductor. The coronary sinus/great vein electrode 8 may be about 5 cm in length.

An implantable pacemaker/cardioverter/defibrillator 10 is shown in combination with the leads, with the lead connector assemblies 4, 13 and 14 inserted into the connector block 12. Optionally, insulation of the outward facing portion of the housing 11 of the pacemaker/cardioverter/defibrillator 10 may be provided using a plastic coating, for example parylene or silicone rubber, as is currently employed in some unipolar cardiac pacemakers. However, the outward facing portion may instead be left uninsulated, or some other division between insulated and uninsulated portions may be employed. The uninsulated portion of the housing 11 optionally serves as a subcutaneous defibrillation electrode, used to defibrillate either the atria or ventricles.

Figure 2:
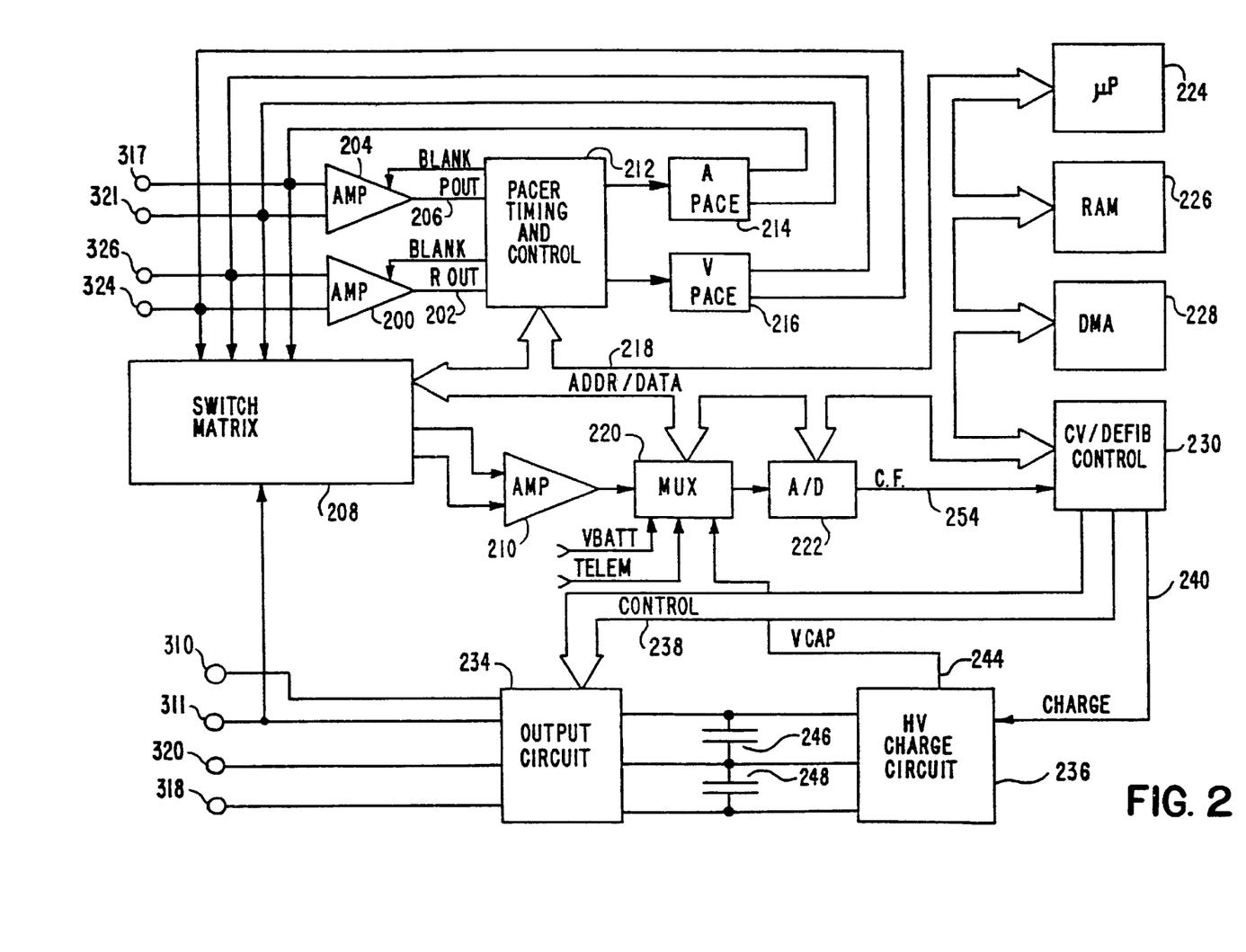
FIG. 2 illustrates a functional schematic diagram of an implantable pacemaker/cardioverter/defibrillator in which the invention may usefully be practiced in conjunction with the electrodes illustrated in FIG. 1.

FIG. 2 is a functional schematic diagram of an implantable pacemaker/cardioverter/defibrillator in which the present invention may usefully be practiced. This diagram should be taken as exemplary of the type of device in which the invention may be embodied, and not as limiting, as it is believed that the invention may usefully be practiced in a wide variety of device implementations, including pacemakers which do not provide cardioversion or defibrillation therapies.

The device is provided with an electrode system including electrodes as illustrated in FIG. 1. Optional electrode 310 corresponds to electrode 11, and is the uninsulated portion of the housing of the implantable pacemaker/cardioverter/defibrillator. Electrode 320 corresponds to electrode 20 and is a defibrillation electrode located in the right ventricle. Electrode 311 corresponds to electrode 23, and is located in the right atrium and SVC. Electrode 318 corresponds to electrode 8 and is a defibrillation electrode located in the coronary sinus and great vein. Electrodes 324 and 326 correspond to electrodes 24 and 26, and are used for sensing and pacing in the ventricle. Electrodes 317 and 321 correspond to electrodes 17 and 21 and are used for pacing and sensing in the atrium.

Electrodes 310, 311, 318 and 320 are coupled to high voltage output circuit 234. High voltage output circuit 234 includes high voltage switches controlled by CV/defib control logic 230 via control bus 238. The switches within circuit 234 control which electrodes are employed and which are coupled to the positive and negative terminals of the capacitor bank including capacitors 246 and 248 during delivery of the defibrillation pulses.

Electrodes 324 and 326 are located on or in the ventricle and are coupled to the R-wave amplifier 200, which preferably takes the form of an automatic gain controlled amplifier providing an adjustable sensing threshold as a function of the measured R-wave amplitude. A signal is generated on R-out line 202 whenever the signal sensed between electrodes 312 and 314 exceeds the present sensing threshold.

Electrodes 317 and 321 are located on or in the atrium and are coupled to the P-wave amplifier 204, which preferably also takes the form of an automatic gain controlled amplifier providing an adjustable sensing threshold as a function of the measured P-wave amplitude. A signal is generated on P-out line 206 whenever the signal sensed between electrodes 317 and 321 exceeds the present sensing threshold. The general operation of the R-wave and P-wave amplifiers 200 and 204 may correspond to that disclosed in U.S. Pat. No. 5,117,824, by Keimel, et al., issued Jun. 2, 1992, for an Apparatus for Monitoring Electrical Physiologic Signals, incorporated herein by reference in its entirety.

Switch matrix 208 is used to select which of the available electrodes are coupled to wide band (0.5–200 Hz) amplifier 210 for use in digital signal analysis. Selection of electrodes is controlled by the microprocessor 224 via data/address bus 218, which selections may be varied as desired. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to generally circuitry known in the prior art, with the addition of the present invention. An exemplary apparatus is disclosed of accomplishing pacing, cardioversion and defibrillation functions follows. The pacer timing/control circuitry 212 includes programmable digital counters which control the basic time intervals associated with DDD, VVI, DVI, VDD, AAI, DDI and other modes of single and dual chamber pacing well known to the art. Circuitry 212 also controls escape intervals associated with anti-tachyarrhythmia pacing and stimulation for purposes of electrophysiologic screwing in both the atrium and the ventricle, employing any anti-tachyarrhythmia pacing therapies known to the art.

Intervals defined by pacing circuitry 212 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 224, in response to stored data in memory 226 and are communicated to the pacing circuitry 212 via address/data bus 218. Pacer circuitry 212 also determines the amplitude of the cardiac pacing pulses under control of microprocessor 224.

During pacing, the escape interval counters within pacer timing/control circuitry 212 are reset upon sensing of R-waves and P-waves as indicated by a signals on lines 202 and 206, and in accordance with the selected mode of pacing on time-out trigger generation of pacing pulses by pacer output circuitry 214 and 216, which are coupled to electrodes 317, 321, 324 and 326. The escape interval counters are also reset on generation of pacing pulses, and thereby control the basic timing of cardiac pacing functions, including anti-tachyarrhythmia pacing. The durations of the intervals defined by the escape interval timers are determined by microprocessor 224, via data/address bus 218. The value of the count present in the escape interval counters when reset by sensed R-waves and P-waves may be used to measure the durations of R-R intervals, P-P intervals, P-R intervals and R-P intervals, which measurements are stored in memory 226 and used to detect the presence of tachyarrhythmias.

Microprocessor 224 operates under control of programmed commands stored in the ROM included therein and operates as an interrupt driven device, responsive to interrupts from pacer timing/control circuitry 212 corresponding to the occurrence sensed P-waves and R-waves and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts. The running interval total employed by the microprocessor to determine times of delivery of ventricular pacing pulses may be stored in RAM 226, with timers within the pacer timing/control circuitry 212 employed to time the A-A intervals separating delivered high rate atrial pacing pulses and the short ventricular escape interval following delivery of the atrial pacing pulse in conjunction with which the running interval total exceeds the desired ventricular escape interval for back-up pacing.

In response to a sensed or paced ventricular depolarization or R-wave, the intervals separating that R-wave from the immediately preceding R-wave, paced or sensed (R-R interval) and the interval separating the paced or sensed R-wave from the preceding atrial depolarization, paced or sensed (P-R interval) may be stored in memory 226. Similarly, in response to the occurrence of a sensed or paced atrial depolarization (P-wave), the intervals separating the sensed P-wave from the immediately preceding paced of sensed atrial contraction (P-P Interval) and the interval separating the sensed P-wave from the immediately preceding sensed or paced ventricular depolarization (R-P interval) may be stored. Preferably, a portion of the memory 226 (FIG. 4) is configured as a plurality of recirculating buffers, capable of holding a preceding series of measured intervals, which may be analyzed in response to the occurrence of a pace or sense interrupt to determine whether the patient's heart is presently exhibiting atrial or ventricular tachyarrhythmia.

Detection of atrial or ventricular tachyarrhythmias, as employed in the present invention, may correspond to tachyarrhythmia detection algorithms known to the art. For example, presence of atrial or ventricular tachyarrhythmia may be confirmed by means of detection of a sustained series of short R-R or P-P intervals of an average rate indicative of tachyarrhythmia or an unbroken series of short R-R or P-P intervals. The suddenness of onset of the detected high rates, the stability of the high rates, or a number of other factors known to the art may also be measured at this time. Appropriate ventricular tachyarrhythmia detection methodologies measuring such factors are described in U.S. Pat. No. 4,726,380, issued to Vollmann, U.S. Pat. No. 4,880,005, issued to Pless et al. and U.S. Pat. No. 4,830,006, issued to Haluska et al., all incorporated herein by reference in their entireties. An additional set of tachycardia recognition methodologies is disclosed in the article "Onset and Stability for Ventricular Tachyarrhythmia Detection in an Implantable Pacer-Cardioverter-Defibrillator" by Olson et al., published in *Computers in Cardiology*, Oct. 7–10, 1986, IEEE Computer Society Press, pages 167–170, also incorporated herein in its entirety. However, one of the advantages of the present invention is that it is believed practicable in conjunction with most prior art tachycardia detection algorithms. Atrial tachycardia and fibrillation detection methodologies in particular are disclosed in U.S. Pat. No. 5,546,186, issued to Olson et al., Published PCT application Ser. No. US92/02829, Publication No. WO92/18198, by Adams et al., and in the article "Automatic Tachycardia Recognition", by Arzbaecher et al., published in PACE, May–June, 1984, pp. 541–547, all of which are incorporated by reference in their entireties.

In the event that an atrial or ventricular tachyarrhythmia is detected, and an anti-tachyarrhythmia pacing regimen is desired, appropriate timing intervals for controlling generation of anti-tachyarrhythmia pacing therapies are loaded from microprocessor 224 into the pacer timing and control circuitry 212, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are incorporated herein by reference in their entireties may also be used.

In the event that generation of a cardioversion or defibrillation pulse is required, microprocessor 224 employs an escape interval counter to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246 and 248 via charging circuit 236, under control of high voltage charging control lines 240 and 242. The voltage on the high voltage capacitors is monitored via VCAP line 244, which is passed through multiplexer 220 and in response to reaching a predetermined value set by microprocessor 224, results in generation of a logic signal on Cap Full (CF) line 244, terminating charging. Thereafter, timing of the delivery of the defibrillation or cardioversion pulse is controlled by pacer timing/control circuitry 212. Following delivery of the fibrillation or tachycardia therapy the microprocessor then returns the device to cardiac pacing and awaits the next successive interrupt due to pacing or the occurrence of a sensed atrial or ventricular depolarization.

One embodiment of an appropriate system for delivery and synchronization of ventricular cardioversion and defibrillation pulses and for controlling the timing functions related to them is disclosed in more detail in commonly assigned U.S. Pat. No. 5,188,105 by Keimel, issued Feb. 23, 1993, incorporated herein by reference in its entirety. Embodiments of appropriate systems for delivery and synchronization of atrial cardioversion and defibrillation pulses and for controlling the timing functions related to them are disclosed in more detail in U.S. Pat. No. 5,269,298 by Adams et al., issued Dec. 14, 1993 and in U.S. Pat. No. 4,316,472 by Mirowski et al., issued Feb. 23, 1982, both incorporated herein by reference in their entireties. However, any known cardioversion or defibrillation pulse control circuitry is believed usable in conjunction with the present invention. For example, circuitry controlling the timing and generation of cardioversion and defibrillation pulses as disclosed in U.S. Pat. No. 4,384,585, issued to Zipes on May 24, 1983, in U.S. Pat. No. 4,949,719 issued to Pless et al., cited above, and in U.S. Pat. No. 4,375,817, issued to Engle et al., all incorporated herein by reference in their entireties may also be employed.

In the illustrated device, delivery of the cardioversion or defibrillation pulses is accomplished by output circuit 234, under control of control circuitry 230 via control bus 238. Output circuit 234 determines whether a monophasic or biphasic pulse is delivered, the polarity of the electrodes and which electrodes are involved in delivery of the pulse. Output circuit 234 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above cited patent issued to Mehra and in U.S. Pat. No. 4,727,877, incorporated by reference in its entirety.

An example of circuitry which may be used to control delivery of monophasic pulses is set forth in commonly assigned U.S. Pat. No. 5,163,427, by Keimel, issued Nov. 17, 1992, also incorporated herein by reference in its entirety. However, output control circuitry as disclosed in U.S. Pat. No. 4,953,551, issued to Mehra et al. on Sep. 4, 1990 or U.S. Pat. No. 4,800,883, issued to Winstrom on Jan. 31, 1989 both incorporated herein by reference in their entireties, may also be used in conjunction with a device embodying the present invention for delivery of biphasic pulses.

In the event that, as in FIG. 1, both atrial and ventricular defibrillation are available, ventricular defibrillation may be accomplished using higher pulse energy levels than required for atrial defibrillation and may employ the same or a different electrode set. For example, electrodes 310, 311, 318 and 320 or only electrodes 311, 318 and 320 may be employed for atrial defibrillation. Electrodes 311, 320 and 310 might be employed for ventricular defibrillation, with electrode 311 (right atrium/SVC) coupled to electrode 310 (device housing). Alternatively, electrodes 310, 318 and 320 may be employed, with electrode 318 (coronary sinus/great vein) coupled to electrode 310. As a further alternative, electrodes 311, 310, 318 and 320 might all be employed for ventricular defibrillation, with electrodes 310, 311 and 320 coupled in common. As yet another alternative, only electrodes 310 and 320 might be employed for ventricular defibrillation. added or substituted for either of electrodes 311 or 318 for treating ventricular fibrillation.

In modern implantable cardioverter/defibrillators, the particular therapies are programmed into the device ahead of time by the physician, and a menu of therapies is typically provided. For example, on initial detection of an atrial or ventricular tachycardia, an anti-tachycardia pacing therapy may be selected and delivered to the chamber in which the tachycardia is diagnosed or to both chambers. On redetection of tachycardia, a more aggressive anti-tachycardia pacing therapy may be scheduled. If repeated attempts at anti-tachycardia pacing therapies fail, a higher level cardioversion pulse may be selected thereafter. Therapies for tachycardia termination may also vary with the rate of the detected tachycardia, with the therapies increasing in aggressiveness as the rate of the detected tachycardia increases. For example, fewer attempts at anti-tachycardia pacing may be undertaken prior to delivery of cardioversion pulses if the rate of the detected tachycardia is above a preset threshold. The references cited above in conjunction with descriptions of prior art tachycardia detection and treatment therapies are applicable here as well.

In the event that atrial or ventricular fibrillation is identified, the typical therapy will be delivery of a high amplitude defibrillation pulse, typically in excess of 10 joules in the case of ventricular fibrillation and about 1 joule or less in the case of atrial defibrillation. Lower energy levels will be employed for cardioversion. As in the case of currently available implantable pacemakers/cardioverter/defibrillators, and as discussed in the above-cited references, it is envisioned that the amplitude of the defibrillation pulse may be incremented in response to failure of an initial pulse or pulses to terminate fibrillation. Prior art patents illustrating such pre-set therapy menus of anti-tachyarrhythmia therapies include the above-cited U.S. Pat. No. 4,830,006, issued to Haluska, et al., U.S. Pat. No. 4,726,380, issued to Vollmann et al. and U.S. Pat. No. 4,587,970, issued to Holley et al.

Figure 3:
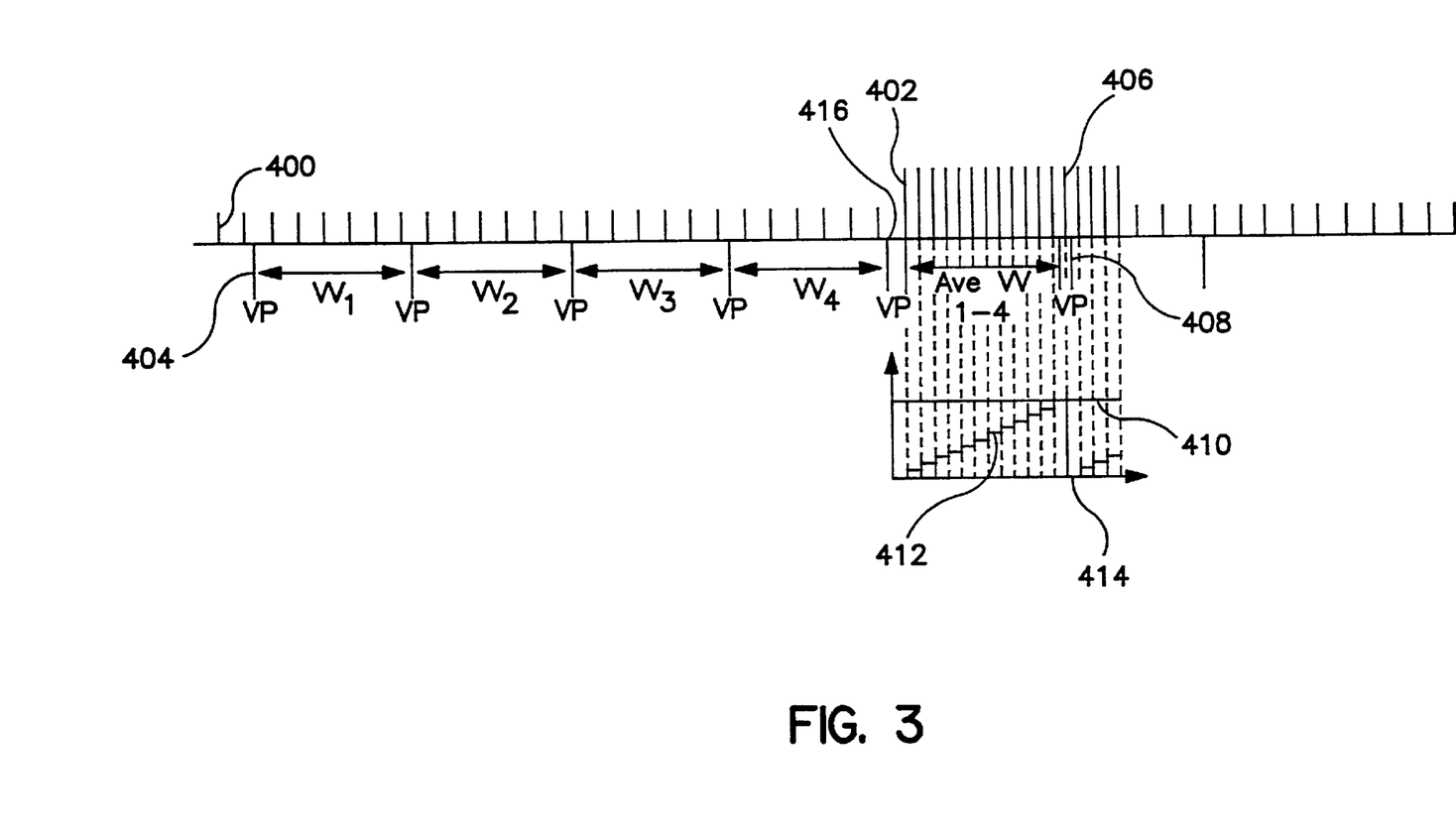
FIG. 3 illustrates a first ventricular back-up pacing modality during atrial high rate pacing.

FIG. 3 is a timing diagram illustrating operation of a device embodying the present invention in the VOO mode. On the timing diagram illustrated, sensed atrial events are indicated by short upwardly extending lines as illustrated at 400, while ventricular pacing pulses are illustrated by longer downwardly extending lines as illustrated at 404. Delivered atrial pacing pulses are illustrated by longer, upwardly extending lines as illustrated at 402. A scan of atrial high rate pacing pulses beginning with pulse 402 is scheduled to begin following the delivery of a ventricular pacing pulse at 416. The duration of the preceding four V-V intervals, including $VV_1$, $VV_2$, $VV_3$ and $VV_4$ is averaged to determine a desired escape interval for ventricular backup pacing, designated Ave $VV_{1-4}$. The desired escape interval 410 for back-up pacing is set as a target, and a running total 412 of A-A intervals is updated by the microprocessor and stored in memory with each delivered atrial pacing. The running total includes the initial R-P interval separating pacing pulses 416 and 402. When the running total 412 of A-A intervals equals or exceeds the desired escape interval 410, the running total is reset to zero at 414 following the delivery of high rate atrial pacing pulse 406. A short escape interval, e.g. 10–30 milliseconds is initiated on delivery of atrial pacing pulse 406 and on expiration of this short escape interval, a ventricular pacing pulse 408 is delivered, synchronizing the ventricular pacing pulse to atrial pacing pulse 406. This process continues until delivery of the last high rate atrial pacing pulse.

In the timing diagram illustrated in FIG. 3, all four ventricular events preceding delivery of the high rate atrial pacing pulse train initiated with pulse 402 are paced ventricular events. As discussed above, in the event that a predetermined number, percentage or pattern of the preceding ventricular events do not meet the criteria for required occurrences of paced ventricular events, delivery of VOO backup ventricular pacing during high rate atrial pacing is disabled. In the specific example illustrated in FIG. 3, four of the preceding four ventricular events must be paced in order to allow back-up ventricular pacing. Alternatively, for example, the device might require that four of the preceding five ventricular events were paced and/or that the preceding five ventricular events included at least three successive paced events.

Figure 4:
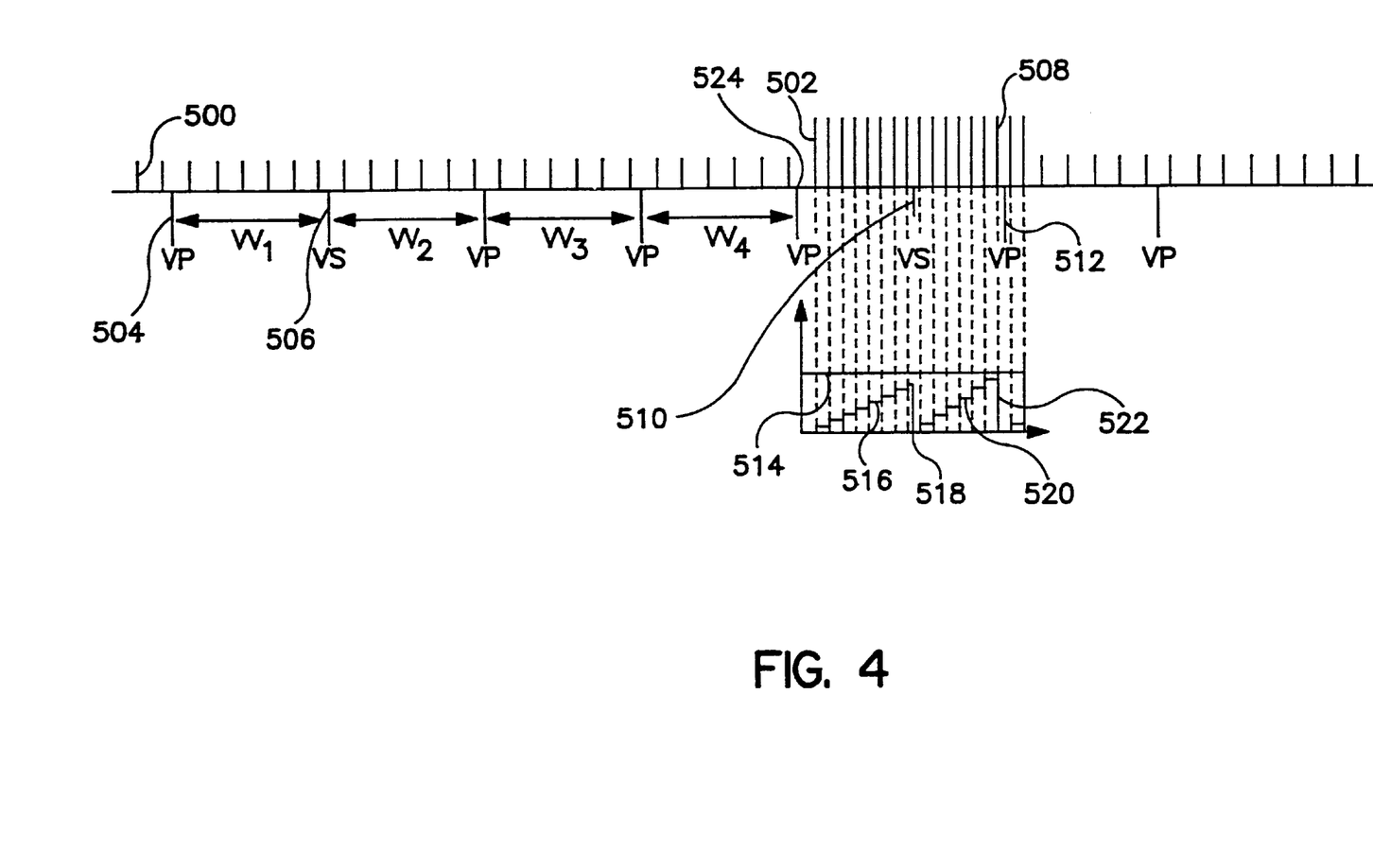
FIG. 4 illustrates a second ventricular back-up pacing modality during atrial high rate pacing.

FIG. 4 illustrates the operation of a device according to the present invention in VVI mode. In the embodiment illustrated, the device does not require that any particular percentage of the preceding ventricular events are paced events as a prerequisite to back-up ventricular pacing. However, it should also be understood that the VVI back-up pacing mode may instead be preconditioned on the occurrence of a predetermined number, percentage or pattern of preceding paced ventricular events, just as in the case of the VOO back-up pacing mode described above. In commercial devices it is anticipated that this option will be programmable by the physician.

The shorter upwardly extending lines corresponding to line 500 are indicative of sensed atrial events, while the longer upwardly extending lines as at 502 are indicative of delivered atrial pacing pulses. Similarly, the shorter, downwardly extending lines as at 506 are indicative of sensed ventricular events, while the longer downwardly extending lines as at 504 are indicative of ventricular pacing pulses. In the timing diagram illustrated a sensed ventricular event occurs at 506. However, as the device is operating in VVI mode during backup ventricular pacing, the occurrence of one or more sensed ventricular events prior to high rate atrial pacing does not inhibit delivery of ventricular backup pacing during the high rate atrial pacing.

Following delivery of a ventricular pacing pulse at 504, the device employs a desired ventricular escape interval programmed by the physician, illustrated at 514. The running total 516 of A-A intervals is incremented with each delivered atrial pacing pulse as in the VOO mode discussed above. At 510, a sensed ventricular event occurs prior to the total 516 equaling or exceeding the desired number escape interval 514, resetting the running total to zero at 518. Incrementing of the running total is resumed at 520, and on equaling or exceeding the desired escape interval 514 of delivered atrial pacing pulses is reset at 522 following delivery of atrial pacing pulse 508. Ten to 30 milliseconds thereafter, a ventricular pacing pulse is triggered at 512.

Figure 5:
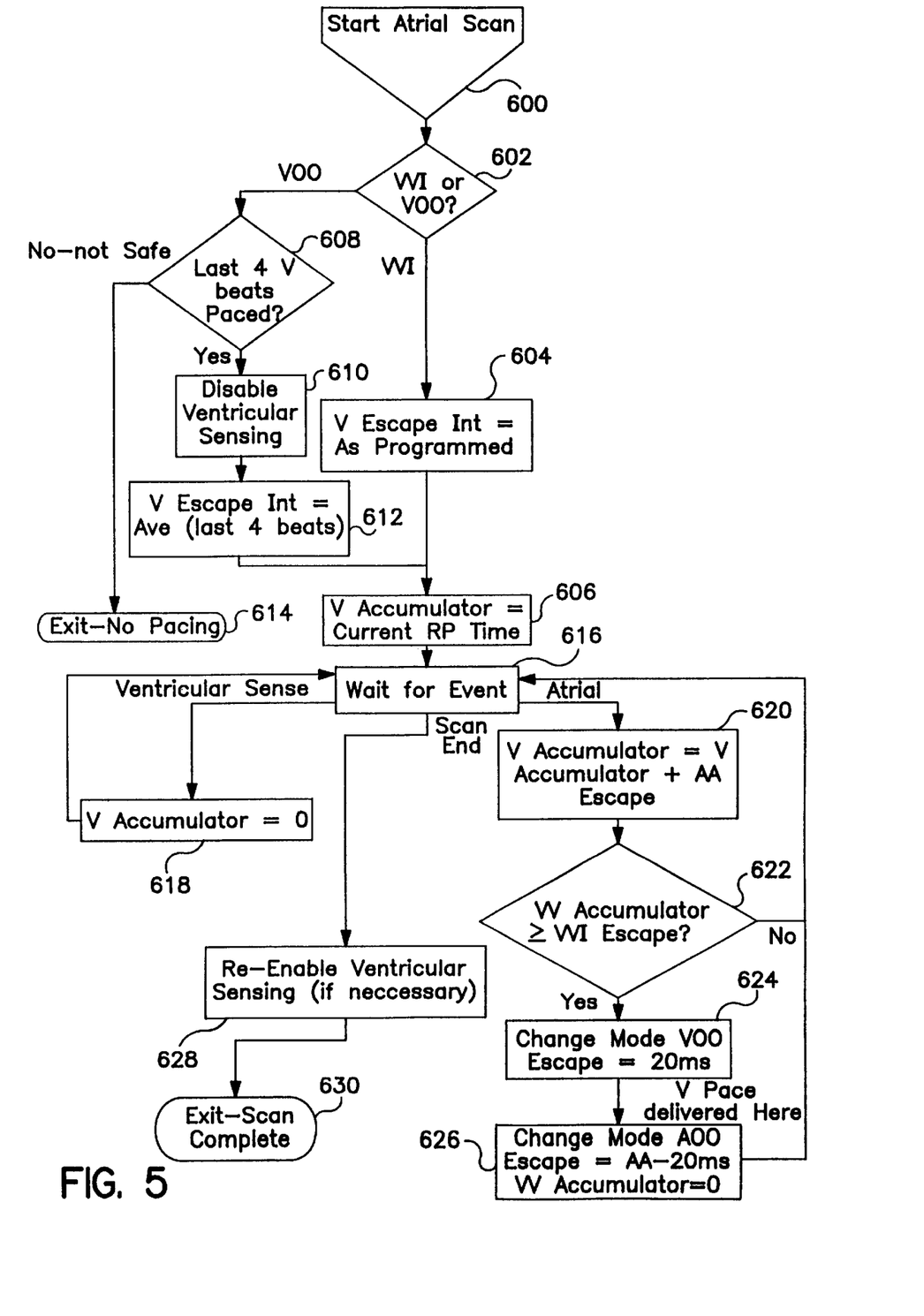
FIG. 5 is a flow chart illustrating the operation of the first and second ventricular back-up pacing modes.

FIG. 5 is a flow chart illustrating operation of a device according to the present invention. High rate atrial pacing is initiated at 600 with delivery of the first atrial pulse, and the device first checks to determine whether ventricular backup pacing is to be delivered in VVI or VOO mode at 602. If backup pacing is to be delivered in VOO mode, the device checks at 608 to determine whether the last four ventricular events were all paced events. If not, backup ventricular pacing is disabled at 614.

If the last four ventricular events prior to initiation of atrial high rate pacing were all paced, the microprocessor disables ventricular sensing at 610 converting the operation of the ventricular pacing mode to asynchronous and calculates the average V-V interval between the preceding four beats at 612. This average is used to determine the desired escape interval which may correspond to the average interval, or as noted above, may correspond to the average interval minus a preset decrement.

In the event that the device is determined to be in VI operation for ventricular backup pacing at 602, the desired ventricular escape interval is set to a physician programmed V-V escape interval. At 606, in response to delivery of the first high rate atrial pacing pulse, the running total of A-A intervals (referred to as the "V accumulator") is set equal to the R-P interval preceding the initial atrial pacing pulse. In the embodiment illustrated, the device does not require that any particular percentage of the preceding ventricular events are paced events as a prerequisite to back-up ventricular pacing. However, it should also be understood that if VVI back-up pacing mode is instead to be preconditioned on the occurrence of a predetermined number or percentage of preceding paced ventricular events, the device could instead perform the operations illustrated at 608 and 610 prior to determining whether the back-up pacing mode is VOO or VVI at 602.

At 616 the processor waits for the next subsequent ventricular event. If a ventricular sense event occurs (which can only happen in VVI mode) the running total of A-A intervals is reset to zero at 618 and the microprocessor continues to wait for the next event. In response to each delivered atrial pacing pulse, the running total of A-A intervals is incremented at 620 by adding the A-A escape interval preceding the delivered atrial pacing pulse and the running total is compared to the desired escape interval at 622. If the running total is greater than or equal to the desired escape interval, the microprocessor temporarily changes the mode of the pacemaker to VOO mode and sets a short escape interval as discussed above. In this case, the short escape interval chosen is 20 milliseconds. On expiration of a short escape interval, a ventricular pacing pulse is delivered, the microprocessor returns the device to AOO mode, setting the escape interval for delivery of the next subsequent atrial pacing pulse equal to the programmed A-A escape interval minus the short 20 millisecond ventricular escape interval, and resets the running total of A-A intervals to zero. If, on occurrence of an atrial pacing pulse, the running total of A-A intervals is not greater than or equal to the desired escape interval, the microprocessor awaits the occurrence of the next subsequent event at 616. This process continues until the occurrence of either a ventricular sense event (in VVI mode) or delivery of the final high rate atrial pacing pulse. Following delivery of the final high rate atrial pacing pulse, ventricular sensing is re-enabled at 628, if the backup ventricular pacing mode was VOO, and the device returns to normal operation in the programmed bradycardia pacing mode at 630.

Figure 6:
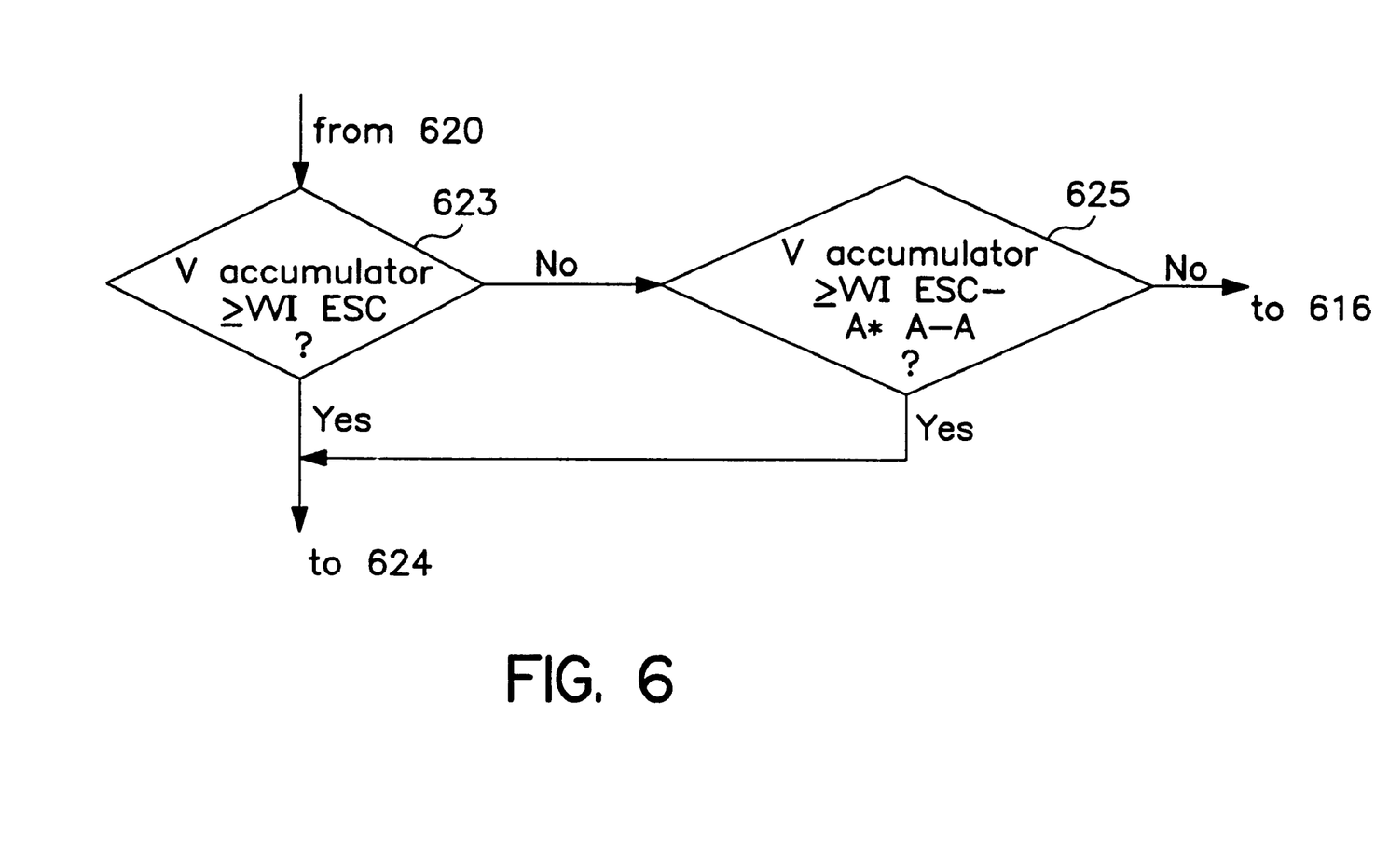
FIG. 6 is a flow chart illustrating an alternative embodiment of the operation of the ventricular back-up pacing modes.

FIG. 6 illustrates an alternative method of operation of a device according to the present invention. FIG. 6 is a modification to the flow chart of FIG. 5 and should be reviewed in conjunction therewith. In the method of operation discussed above in conjunction with FIG. 5, if a sensed atrial depolarization closely precedes the specified ventricular escape interval, delivery of a ventricular pacing pulse must await the occurrence of the next subsequent atrial pacing pulse, and expiration of the short VOO escape interval thereafter. In some cases, this may lead to an interval between delivered backup ventricular pacing pulses which is substantially in excess of the desired escape interval. The alternative embodiment of FIG. 6 is directed toward preventing such prolonged V-V intervals.

In the context of a device operating according to FIG. 6, after sensing an atrial depolarization at 616 (FIG. 5) and incrementing the V accumulator value at 620 (FIG. 5), at 622, the device compares the value of the V accumulator to the desired ventricular escape interval, and, if the value is greater than or equal to the desired ventricular escape interval, proceeds to initiate timing of the short VOO escape interval at 624 as described above as described above. If, however, the value of the V accumulator is less than the desired ventricular escape interval, the device checks at 623 to determine whether the value of the V accumulator is less than the desired ventricular escape interval minus a preset percentage "A" (e.g. 50%) of the A-A pacing interval then in effect. If so, the device initiates time of the short VOO escape interval at 624 (FIG. 5). Otherwise, the device awaits the occurrence of the next sensed event at 616 (FIG. 5).

By means of the method illustrated in FIG. 6, the device avoids excessively prolonged V-V intervals by triggering initiation of the short VOO escape interval following delivered atrial pacing pulses occur very close to, but prior to, expiration of the desired V-V interval. In a device employing the improvement of FIG. 6, the displayed V-V escape interval may be slightly less than or slightly more than the desired V-V escape interval, but will display a maximum variance from the desired V-V escape interval less than would be possible in conjunction with a device operating according to the methodology displayed in FIG. 5 alone.

The present invention as disclosed above takes the form of a microprocessor control device, operating under control of stored software. However, it should be understood that the present invention may also be embodied in the context of a full custom digital integrated circuit, specifically configured to perform the same functions as described above. Similarly, while the invention is disclosed in conjunction with a implantable atrial-ventricular defibrillator, the invention may also be useful in conjunction with anti-tachyarrhythmia pacemakers which do not include defibrillation capabilities, and in conjunction with implantable pacemaker/defibrillators having the ability to defibrillate in only the atria or in only the ventricles. As such, the above described embodiments should be considered exemplary rather than limiting in conjunction with the following claims.

In conjunction with the above specification, we claim:

1. An atrial and ventricular pacemaker, comprising:
   an atrial pulse generator;
   a ventricular pulse generator; and
   a timing and control circuit coupled to said atrial and ventricular pulse generators and controlling timing of atrial and ventricular pacing pulses, said timing and control circuit comprising:
   means for triggering delivery of high rate atrial pacing pulses;
   means for defining a criterion based on occurrences of paced ventricular events prior to delivery of high rate atrial pacing pulses;
   means for determining whether paced ventricular events preceding delivery of high rate atrial pacing pulses meet said criterion; and
   means for delivering ventricular pacing pulses during delivery of high rate atrial pacing pulses in response to a determination that said paced ventricular events preceding delivery of high rate atrial pacing pulses meet said criterion.

2. A pacemaker according to claim 1, wherein said criterion is that all of a series of preceding ventricular events were paced.

3. A pacemaker according to claim 1, wherein said criterion is that a required percentage of a series of preceding ventricular events were paced.

4. A pacemaker according to claim 1 or claim 2 or claim 3 wherein said means for delivering ventricular pacing pulses comprises means for delivering ventricular pacing pulses in VOO mode.

5. A pacemaker according to claim 1 or claim 2 or claim 3 wherein said means for delivering ventricular pacing pulses comprises means for delivering ventricular pacing pulses in VVI mode.

6. An atrial and ventricular pacemaker, comprising:
   an atrial pulse generator;
   a ventricular pulse generator; and
   a control and timing circuit coupled to the atrial and ventricular pacing pulse generators and controlling timing and delivery of atrial and ventricular pacing pulses, the timing and control circuit comprising:
   means for triggering delivery of high rate atrial pacing pulses;
   means for defining a desired ventricular escape interval, during delivery of atrial high rate pacing pulses;
   means for accumulating a running total of A-A intervals separating high rate atrial pacing pulses;
   means for comparing said running total of A-A intervals to said desired ventricular escape interval; and
   means responsive to said running total of A-A intervals exceeding said desired ventricular escape interval for triggering delivery of a ventricular pacing pulse.

7. An atrial and ventricular pacemaker, comprising:
   an atrial pulse generator;
   a ventricular pulse generator; and
   a control and timing circuit coupled to the atrial and ventricular pacing pulse generators and controlling timing and delivery of atrial and ventricular pacing pulses, the timing and control circuit comprising:
   means for triggering delivery of high rate atrial pacing pulses;
   means for defining a desired ventricular escape interval, during delivery of atrial high rate pacing pulses;
   means for accumulating a running total of A-A intervals separating high rate atrial pacing pulses;
   means for comparing said running total of A-A intervals to said desired ventricular escape interval; and
   means responsive to said running total of A-A intervals having less than a defined difference from said desired ventricular escape interval for triggering delivery of a ventricular pacing pulse.

8. An atrial and ventricular pacemaker according to claim 6 or claim 7, wherein said defining means comprises means for determining V-V interval durations separating ventricular events preceding delivery of high rate atrial pacing and means for defining said desired ventricular escape interval as a function of said V-V interval durations.

9. An atrial and ventricular pacemaker according to claim 6 or claim 7, wherein said control and timing circuitry comprises means for synchronizing ventricular pacing pulses delivered during high rate atrial pacing to delivered high rate atrial pacing pulses.

10. An atrial and ventricular pacemaker according to claim 9 wherein said synchronizing means comprises means for defining a short escape interval following delivery of a high rate atrial pacing pulse and means for delivering a ventricular pacing pulse on expiration of said short escape interval.

11. A method of atrial and ventricular pacing, comprising:
   delivering of high rate atrial pacing pulses;
   defining a criterion based on occurrences of paced ventricular events prior to delivery of high rate atrial pacing pulses;
   determining whether paced ventricular events preceding delivery of high rate atrial pacing pulses meet said criterion; and
   delivering ventricular pacing pulses during delivery of high rate atrial pacing pulses in response to a determination that said paced ventricular events preceding delivery of high rate atrial pacing pulses meet said criterion.

12. A method according to claim 11, wherein said defining step comprises defining a criterion that all of a series of preceding ventricular events were paced.

13. A method according to claim 11, wherein said defining step comprises defining a criterion that a required percentage of a series of preceding ventricular events were paced.

14. A method according to claim 11 or claim 12 or claim 13 comprising delivering said ventricular pacing pulses in VOO mode.

15. A method according to claim 11 or claim 12 or claim 13 comprising delivering said ventricular pacing pulses in VVI mode.

16. A method of atrial and ventricular pacing, comprising:
   delivering high rate atrial pacing pulses;
   defining a desired ventricular escape interval, during delivery of atrial high rate pacing pulses;
   accumulating a running total of A-A intervals separating high rate atrial pacing pulses;
   comparing said running total of A-A intervals to said desired ventricular escape interval; and
   responsive to said running total of A-A intervals exceeding said desired ventricular escape interval, delivering a ventricular pacing pulse.

17. A method of atrial and ventricular pacing, comprising:
   delivering high rate atrial pacing pulses;
   defining a desired ventricular escape interval, during delivery of atrial high rate pacing pulses;
   accumulating a running total of A-A intervals separating high rate atrial pacing pulses;
   comparing said running total of A-A intervals to said desired ventricular escape interval; and
   responsive to said running total of A-A intervals having less than a defined difference from said desired ventricular escape interval, delivering a ventricular pacing pulse.

18. A method according to claim 16 or claim 17, wherein said defining step comprises determining V-V interval durations separating ventricular events preceding delivery of high rate atrial pacing and defining said desired ventricular escape interval as a function of said V-V interval durations.

19. A method according to claim 16 or claim 17, comprising delivering said ventricular pacing pulses synchronized to said high rate atrial pacing pulses.

20. A method according to claim 19 comprising defining a short escape interval following delivery of a high rate atrial pacing pulse and delivering a ventricular pacing pulse on expiration of said short escape interval.

* * * * *